(12) United States Patent
Wils et al.

(10) Patent No.: US 7,704,974 B2
(45) Date of Patent: Apr. 27, 2010

(54) METHOD FOR THE TREATMENT AND/OR PREVENTION OF URINARY DISORDERS

(75) Inventors: Daniel Wils, Morbecque (FR); Laëtitia Deremaux, Lille (FR)

(73) Assignee: Roquette Freres, Lestrem (FR)

( * ) Notice: Subject to any disclaimer, the term of this patent is extended or adjusted under 35 U.S.C. 154(b) by 65 days.

(21) Appl. No.: 11/594,194

(22) Filed: Nov. 8, 2006

(65) Prior Publication Data
US 2007/0111966 A1 May 17, 2007

(30) Foreign Application Priority Data
Nov. 9, 2005 (FR) .................... 05 11427

(51) Int. Cl.
*A61K 31/715* (2006.01)
*A01N 43/04* (2006.01)

(52) U.S. Cl. .......................... 514/54; 514/58
(58) Field of Classification Search .................. None
See application file for complete search history.

(56) References Cited

U.S. PATENT DOCUMENTS 4,626,441 A * 12/1986 Wolkstein .................. 426/548

FOREIGN PATENT DOCUMENTS

| EP | 1 006 128 | 6/2000 |
| EP | 1 369 432 | 12/2003 |
| WO | 92/02149 | 2/1992 |
| WO | 00/64281 | 11/2000 |
| WO | 2005/039518 | 5/2005 |

OTHER PUBLICATIONS

Merck Manuals Online Medical Library, Kidney and Urinary Tract Disorders.*
Baxter, Osmitrol Injection.*
Phillips et al. Clin. Endocrinol. (Oxf) Aug. 1994; 207-12, abstract only.*
Loretti et al. Pesquisa Veterinaria Brasileira, 2003, vol. 23, No. 2, pp. 61-64, abstract only.*
Sczcepańska-Sadowska et al. Pflügers Arch. 358, 259-264 (1975).*
Grases et al. Nephron 1998; 78: 296-301.*
Jie et al. Am J Clin Nutr 2000; 72: 1503-9.*
Loretti et al. Pesquisa Veterinaria Brasileira, 2003, vol. 23, No. 2, pp. 61-64.*

* cited by examiner

*Primary Examiner*—Shaojia Anna Jiang
*Assistant Examiner*—Layla Bland
(74) *Attorney, Agent, or Firm*—Young & Thompson

(57) ABSTRACT

The present invention relates to a method for the treatment and/or prevention of urinary disorders, comprising administering an effective amount of an osmotic diuretic agent and an effective amount of an appetence-inducing agent to a subject in need thereof.

15 Claims, No Drawings

METHOD FOR THE TREATMENT AND/OR PREVENTION OF URINARY DISORDERS

FIELD OF THE INVENTION

The invention relates to a method for the treatment and/or prevention of urinary disorders in a subject in need thereof, especially in domestic animals, and in particular in cats, dogs or rats.

BACKGROUND OF THE INVENTION

Domestic animals, and especially cats and dogs, are subject to urinary disorders that may or may not be accompanied by stones, consisting of ammonium magnesium compound phosphates (struvite) or of calcium oxylates.

Cats are physiologically predisposed to having concentrated urine, due to their desert origin and to their relative lack of interest in taking on board water.

In dogs, the recurrence of urinary stones is observed when an intercurrent disease increases the risk of urinary infection, a factor which promotes the formation of struvite stones, or in dogs which do not drink very much.

Kidney stones consist predominantly of calcium salts and more rarely of struvites. The latter can be dissolved by means of a diet that induces an acidic urinary pH (pH less than 6). Calcium oxylate stones are currently impossible to dissolve and they must be extracted from the bladder surgically.

The first recommendation given to individuals suffering from urinary stones is to drink more in order to dilute the urine. This dilution acts at two levels: first, by reducing the electrolyte concentration in the urine, and then by increasing micturition frequency and therefore reducing the amount of time spent by the urine in the bladder.

In animals, the most difficult thing is to increase spontaneous drinking, in particular in cats which generally drink only 30 millilitres of water per kilo of body weight.

The provision of a moist food makes it possible to induce drinking in an animal that does not drink very much, but it is not sufficient, either because it does not cause enough water to be ingested, or because it does not sufficiently increase diuresis.

Animals exhibiting a urological syndrome are often obese or carry excess weight, in particular cats. The provision of fibres in considerable amount in the food is a solution for diluting the energy density of the ingested material, but can increase the share of faecal water rather than the frequency of micturition. Moreover, the provision of a food with a high energy density is not desirable (risk of obesity due to overconsumption) but is currently virtually obligatory so as not to increase faecal water.

Thus, when it is desired to treat or prevent urinary disorders, and in particular recurrences of urolithiasis, the provision of a moist food is preferable, but it is not sufficient, may not be accepted by the animals, or even may induce an additional pathology (excess weight, obesity) if the amount distributed is poorly controlled.

There therefore exists today a need for a composition that promotes the amount of water that is drunk, which would at the same time promote urinary excretion, while at the same time not inducing gastrointestinal problems and allowing dilution of the energy content of the ingested material.

SUMMARY OF THE INVENTION

After numerous research studies the applicant has found that this aim can be achieved by preparing a diuretic and appetence-inducing composition comprising an osmotic diuretic and an appetence-inducing agent, particularly suitable for the treatment or prevention of urinary disorders in domestic animals in that it considerably increases the amount of water spontaneously drunk by the animal, while at the same time promoting urinary excretion, without unbalancing the animal's calorie intake or leading to intestinal problems.

An aspect of the present invention relates to a method for the treatment and/or prevention of urinary disorders, comprising administering a composition comprising an effective amount of a osmotic diuretic agent and an effective amount of an appetence-inducing agent to a subject in need thereof.

An aspect of the present invention relates to a method for the treatment and/or prevention of urinary disorders, comprising administering an effective amount of an osmotic diuretic agent and an effective amount of an appetence-inducing agent to a subject in need thereof.

Another aspect of the invention relates to a kit for the treatment and/or prevention of urinary disorders, comprising:
an osmotic diuretic agent; and
an appetence-inducing agent.

DETAILED DISCLOSURE

In the context of the invention, the term "treating" or "treatment", as used herein, means reversing, alleviating, inhibiting the progress of the disorder or condition to which such term applies, or one or more symptoms of such disorder or condition.

According to the invention, the term "subject in need thereof", is intended for a human or non-human mammal affected or likely to be affected with a urinary disorder.

By "effective amount" is meant a sufficient amount of said compound to treat urinary disorders at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the method of the present invention; and like factors well known in the medical arts. For example, it is well within the skill of the art to start doses of the compound at levels lower than those required to achieve the desired therapeutic effect and to gradually increase the dosage until the desired effect is achieved.

Typically, a composition according to the invention is a low-calorie composition.

It may, for example, be in the form of a drink, a tablet or a powder.

The term "osmotic diuretic" is intended to mean a molecule that acts by increasing the osmolarity of the glomerular filtrate, which brings about a call for water in the nephron and increases the excretion of sodium and chlorine. Osmotic diuretic agents known at the current time are mainly polyols. mannitol, erythritol, arabitol and isosorbide are particularly targeted by the present invention. The diuretic effect of these polyols is known and has been demonstrated. However, they do not by themselves constitute a solution to the problem raised by the applicant, in the sense that they do not stimulate thirst or drinking in animals.

For the purpose of the present invention, the term "appetence-inducing agent" is intended to mean an agent capable of increasing thirst or spontaneous drinking in the animal. This definition relates to indigestible dextrins and polydextrose, which induce, surprisingly and unexpectedly, a greater desire to drink on the part of the animal.

The combination of the diuretic agent and of the appetence-inducing agent according to the invention, as will be demonstrated, moreover, advantageously induces a desire to drink and an increased urine output, while at the same time preserving the animal's energy balance, and also its intestinal comfort.

Typically, the osmotic diuretic agent is a polyol or a mixture of polyols. The polyol or mixture of polyols may be selected from the group consisting of mannitol, erythritol, arabitol, isosorbide, and mixtures thereof.

The appetence-inducing agent may be selected from the group consisting of indigestible dextrins, polydextrose, and mixture thereof.

The diuretic agent/appetence-inducing agent ratio is preferably between 1:50 and 50:1, preferably between 1:20 and 20:1, more preferably between 1:10 and 10:1, and even more preferably between 1:2 and 1:3.

The composition or the various elements of the kit according to the invention are intended to be administered preferably in the form of a drink. According to another variant of the invention, they can be formulated so as to be able to be incorporated into the food intake.

The composition or the various elements of the kit can be in various forms:
a syrup to be reconstituted in water;
a powder, or a tablet, to be diluted in water;
a ready-to-use drink.

Typically, the powder may be enclosed in a sachet.

A diuretic and appetence-inducing drink according to the present invention comprises a mixture of at least one diuretic and osmotic agent and of at least one appetence-inducing agent, in a weight ratio of between 1:50 and 50:1, preferably between 1:20 and 20:1, and even better still between 1:10 and 10:1.

The concentration of this drink will be between 2 and 750 grams of solids per litre of drink, depending on the polyols chosen, the tolerance to said polyols, the animal concerned and its metabolism and weight, and also depending on the tolerance with respect to the appetence-inducing agent.

According to a preferred variant, said drink comprises from 1 to 50 grams per litre of diuretic polyol, preferably from 1 to 40 g/l, and even more preferably from 2 to 10 g/l of drink. Since some polyols are more or less well tolerated depending on the metabolisms and the organisms, the abovementioned concentrations will therefore be adjusted by those skilled in the art so as to observe a suitable tolerance threshold.

The osmotic diuretic agents will be selected from the group consisting of mannitol, erythritol, arabitol or isosorbide, alone or as a mixture thereof.

As regards the appetence-inducing agent, it will be present in the drink in such a way as to observe the abovementioned ratios. By way of example, for an amount of 2 grams per litre of polyol, the drink may comprise from 0.2 to 20 grams of appetence-inducing agent per litre of drink, depending on the desired effect and on the animal concerned.

The appetence-inducing agent will be selected from the group consisting of indigestible dextrins and polydextrose, alone or as a mixture thereof. The indigestible dextrins according to the present invention denote in particular wheat dextrins, maize dextrins, pea dextrins or potato dextrins, obtained by dry roasting of starch in an acidic medium so as to obtain highly branched dextrins, such as in particular those sold under the name Fiberso® by the company Matsutani, or else the branched maltodextrins sold by the applicant and described in Patent EP 1.006.128 (incorporated by reference). Branched maltodextrins having a number-average molecular weight of between 2000 and 3000 grams per mol and a degree of 1→6 glucoside linkages of between 15 and 35% will preferably be used. The present invention also relates to the hydrogenated variants of said indigestible dextrins, and also the syrups of polyols containing same, such as, in particular, maltitol syrups.

Polydextrose is a low-calorie glucose polymer, known to those skilled in the art, and obtained by polycondensation reaction of glucose, maltose, glucose oligomers or starch hydrolysates, in the presence of acid. The term "polydextrose" according to the present invention also comprises the purified and/or hydrogenated variants of polydextrose.

The applicant has demonstrated, in the course of studies in rats in particular, that, surprisingly and unexpectedly, polydextrose and indigestible dextrins very significantly increase the amounts of water drunk by animals. On the other hand, the overconsumption of water, generated by these appetence-inducing agents, did not show any effects on diuresis, but on the solids content of the faeces. The excess water consumed is therefore excreted in the faeces.

On the other hand, if a diuretic agent and an appetence-inducing agent capable of increasing drinking are combined, urinary excretion is then promoted and the technical problem forming the basis of the present invention is solved, all the more advantageously since said combination does not induce any gastrointestinal problems and allows a dilution of the energy content of the ingested material, which constitutes an ideal solution.

When it is chosen to prepare a drink, a concentration of diuretic agent of greater than 1 g/l will preferably be used. Below 1 g/l of diuretic polyol in the composition, the diuretic effect is weak. Above 50 g/l of diuretic polyol, the risks of intestinal problems become non-negligible, this limit depending, however, on the polyol concerned. This concentration will, of course, also be determined according to the tolerance to the polyols of the animal concerned, said tolerance being variable from one species to the other. According to a preferred embodiment, concentrations of between 2 and 10 grams per litre of diuretic polyol will be chosen.

As regards the appetence-inducing agent, it is more effective, as such, from 2 grams per litre; above 20 grams per litre, there is a risk of it leading to intestinal problems (diarrhoea, bloating). Concentrations of between 3 and 15 grams per litre, or better still between 5 and 10 grams per litre, will preferably be chosen.

In cats and dogs, very significant results have been obtained with a drink comprising 2 grams per litre of diuretic polyol and 5 grams per litre of appetence-inducing agent (i.e. a weight ratio of 1:2.5). Very good results are also obtained with weight ratios of between 1:2 and 1:3.

When the composition according to the invention is a concentrated syrup to be reconstituted in water, the syrup will be made to contain the necessary amounts of diuretic agent and of appetence-inducing agent so that the final drink comprises effective proportions of the mixture. This syrup may comprise from 2 to 750 grams per litre, preferably from 2 to 500 g/litre of solids of said diuretic agent/appetence-inducing agent mixture, and those skilled in the art will readily choose, according to the use of said syrup, the proportions that are suitable, taking into account the tolerance thresholds for each compound of the mixture.

By way of example, a concentrated syrup according to the invention, that will be reconstituted at a rate of one volume per 70 volumes of water, will advantageously comprise 140 g/litre of diuretic polyol and 350 g/litre of appetence-inducing agent. 350 ml of drink may, for example, be prepared from 5 ml of syrup according to the invention, which may advantageously correspond to a cap of syrup to be reconstituted in a bottle with a final volume of 350 ml.

The concentrated syrup according to the invention will be sufficiently concentrated to prevent the growth of microorganisms while it is stored. By way of example, it will be necessary to have free water values aw of less than 0.85 or to add a preserving agent. In any event, it will be advisable to observe the polyol/appetence-inducing agent weight ratio of between 1:50 and 50:1, and better still between 1:20 and 20:1.

According to another variant of the present invention, the composition or the various elements of the kit are in the form of a powder or of a tablet to be reconstituted in water or to be mixed in with the food intake.

Such a powder will comprise the abovementioned ratio of polyol and appetence-inducing agent. For example, for a sachet of powder to be reconstituted in 1 litre of water, the dose sachet will comprise from 1 to 4 grams of diuretic polyol and from 2 to 20 grams of appetence-inducing agent. According to a preferred variant, it will comprise 2 grams of polyol and 5 grams of appetence-inducing agent.

Similarly, for the formulation of tablets, tablets comprising a ratio of diuretic polyols to appetence-inducing agent of between 1:50 and 50:1 may be prepared. By way of example, a tablet of 1 gram may comprise 350 mg of polyol and 715 mg of appetence-inducing agent.

Very good results have been obtained with the following compositions:
- 2 g/litre of mannitol and 5 g/litre of indigestible dextrins;
- 2 g/litre of erythritol and 5 g/litre of polydextrose;
- 2 g/litre of isosorbide and 5 g/litre of indigestible dextrins or of polydextrose;
- 2.5 g/litre of arabitol and 5 g/litre of indigestible dextrins or of polydextrose;
- drink comprising a mixture of mannitol and erythritol, and also indigestible dextrins.

Of course, the composition or the various elements of the kit according to the invention may comprise any additive suitable, in particular, for the preparation of drinks, such as flavours, preserving agents, vitamins, minerals or active ingredients, provided that they do not change the nature of the effects of said composition or of said kit.

An aspect of the present invention relates to a method for the treatment and/or prevention of urinary disorders, especially in domestic animals, and in particular for the treatment of urolithiasis. The treatment consists of the administration, to a domestic animal, of an effective amount of diuretic and appetence-inducing composition, in the form of a drink or added to the food intake, so as to stimulate drinking and promote diuresis.

The present invention also encompasses the variant according to which the diuretic agent can be administered simultaneously with, consecutively to or prior to the appetence-inducing agent, for treating or preventing urinary disorders.

It goes without saying that the composition or the kit according to the invention can also find applications in humans, in the sense that the combination of a diuretic agent and of an agent that increases thirst can be used to advantage, besides for the treatment or prevention of urinary disorders, in the formulation of dietetic drinks, in particular for draining, depurative and/or slimming purposes.

The invention will be understood more clearly on reading the following examples, which are meant to be illustrative and non-limiting.

EXAMPLES

Example 1

Influence of the Oral Administration of Erythritol, Mannitol or Isosorbide in Sprague-Dawley Rats A batch of rats were orally administered doses of diuretic polyols so as to measure the diuretic effect of said polyols and their possible influence on the amount of water drunk. The study was carried out on a batch of thirty rats, for 4 days, and the trial doses were administered at a rate of 2 ml per animal and per day of solutions at 250 g/litre of polyols. Water is distributed to the animals ad libitum. The amounts of urine output and of drink consumed are measured by weighing.

The amounts of drink are expressed in grams per animal and per day. Diuresis is expressed in millilitres as a function of time.

Batch A: control batch
Batch B: erythritol gavage
Batch C: mannitol gavage
Batch D: isosorbide gavage
Batch E: 1/1 isosorbide-mannitol mixture CONSUMPTION OF DRINK (Means on Ten Rats)

Batch A: water consumption is 24.8 g per animal and per day (mean of ten trials)

Batch B: water consumption is 17.9 g/animal/day.

After 3 days, the water consumption after erythritol gavage is not greater than the control.

Batch A: over four days, it is 11.2 g/animal/day
Batch C: 13.9
Batch D: 13.1
Batch E: 13.3

The water consumption after mannitol gavage or isosorbide gavage is very slightly greater than the control.

DIURESIS (Means on Ten Rats, in Millilitres)

| Batch | Before gavage | 45 min | 1 h 35 min | 3 h | 5 h | 7 h | Cumulative diuresis over 24 h |
|---|---|---|---|---|---|---|---|
| A | 3.2 | 0.9 | 0.6 | 0.4 | 0.7 | 0.6 | 11.7 |
| B (erythritol) | 1.02 | 0.21 | 0.99 | 1.38 | 1.21 | 0.83 | 18.43 |
| C (mannitol) | 3.0 | 0.3 | 0.3 | 0.7 | 0.5 | 1.3 | 16.5 |
| D (isosorbide) | 2.4 | 1.5 | 1.1 | 1.2 | 1.1 | 0.6 | 13.0 |
| E (mannitol/isosorbide mixture) | 1.85 | 0.5 | 0.46 | 1.08 | 1.35 | 1.63 | 16.16 |

Conclusion: a significant increase in diuresis compared with the control is observed for the trials for gavage with diuretic polyols. In the case of erythritol, an increase in diuresis is observed from 3 hours, whereas it is later for the other polyols (between 3 and 5 hours).

Gavage of the rats with these polyols does not, however, make it possible to significantly increase the amount of water drunk during the trials. It would therefore be necessary to supplement the treatment of the rats with an appetence-inducing agent capable of increasing spontaneous drinking by the rats, to as to compensate for the water losses induced by the diuretic polyols.

Example 2

Study of the Effects of the Administration of Indigestible Dextrin in Rats

Increasing doses of Nutriose® FB (sold by the applicant) of from 1.25% to 5% by weight are incorporated into the food of rats. The study is carried out on 50 obese males and on 50 control males.

The animals are monitored for 46 weeks, during which time drink and food consumptions are measured.

Control Rats: Mean Total Consumption of Drink in Grams Per Animal at the End of the Study:
control: 5360.3
1.25% Nutriose® FB: 5251.0
2.5% Nutriose® FB: 5637.2
5% Nutriose® FB: 5776.3
Obese Rats:
control: 6206.3
1.25% Nutriose® FB: 6885.6
2.5% Nutriose® FB: 6283.8
5% Nutriose® FB: 6851.0

Conclusion: the rats treated with 5% of Nutriose® FB consume more water than the control rats (7% more). Those treated with 2.5% of Nutriose® FB consume 5% more water.

In the obese rat, this difference is even more marked (increase of 10 to 12%).

It clearly appears that the treatment of the rats with Nutriose® FB induces a greater consumption of water compared with the control. The obese rats consume more water than the control rats, which is in part explained by the greater consumption of food by the latter.

Example 3

Study of the Effects of the Administration of Polydextrose in Rats

As for the preceding trial, polydextrose Litesse® (Pfizer), Nutriose® FB06 (wheat dextrin) and Nutriose® FM06 (maize dextrin) are incorporated into the food of Sprague-Dawley rats for 21 days. The doses incorporated for each compound are 1.25, 2.5 and 5%.

In the same way, the total consumption of drink during the study is measured and expressed in grams per animal.

Results:
control: 484.0
1.25% Nutriose® FB06: 514.9
2.5% Nutriose® FB06: 494.6
5% Nutriose® FB06: 503.8
1.25% Nutriose® FM06: 515.6
2.5% Nutriose® FM06: 520.7
5% Nutriose® FM06: 529.0
1.25% Litesse®: 576.8
2.5% Litesse®: 542.4
5% Litesse®: 582.7

The introduction of polydextrose into the food of the rats leads to a significant increase in water consumption over time and over the entire study.

The rats treated with Nutriose® also see their water consumption increased compared with the control, but less markedly. However, the greater water consumptions do not induce an increase in diuresis. On the other hand, the study demonstrated that the solids content of the faeces decreased in the course of the study, which demonstrates that the overconsumption of water is compensated for by elimination thereof in the faeces and not via the urine.

The indigestible dextrins and the polydextrose manifestly and surprisingly induce an increase in drinking by the rats, but have no effect on diuresis.

Example 4

Study of the Effects of the Administration of Mixtures of Appetence-Inducing Agent and of Diuretic Agent Mixtures of diuretic polyols and of appetence-inducing agents are administered to a batch of rats, in the drink. The aim of this study is to measure the diuretic effect of these polyols and the influence of the appetence-inducing agent on the amount of drink consumed and the volume of urine excreted. The study is carried out on batches of 10 rats, each for 3 days. The products tested are administered at a rate of 50 g/l for the appetence-inducing agent and 25 g/l for the polyols. This drink is left available to the animals ad libitum. The drink consumed is measured by weighing on each day of the study and is expressed in grams as a function of time. The diureses are expressed in millilitres.

Batch Organization:
batch 1: control
batch 2: polydextrose/erythritol
batch 3: Nutriose® FB17/erythritol
batch 4: Nutriose® FB17/mannitol Consumption of Drink (Means on Ten Rats):

|  | D0 to D1 | D1 to D2 | D2 to D3 | Total | % evolution compared with the control |
|---|---|---|---|---|---|
| Batch 1 | 27.6 | 30.2 | 30.1 | 87.9 | — |
| Batch 2 | 39.9 | 34.1 | 38.5 | 112.4 | +27% |
| Batch 3 | 39.8 | 37.3 | 40.2 | 117.4 | +33% |
| Batch 4 | 35.4 | 30.7 | 31.4 | 97.5 | +10% |

Diureses (Means on Ten Rats):

|  | D0 to D1 | D1 to D2 | D2 to D3 | Total | % evolution compared with the control |
|---|---|---|---|---|---|
| Batch 1 | 6.7 | 8.0 | 7.6 | 22.4 | — |
| Batch 2 | 10.4 | 9.6 | 5.6 | 25.6 | +14% |
| Batch 3 | 12.5 | 12.4 | 9.8 | 34.7 | +54% |
| Batch 4 | 10.0 | 9.5 | 6.9 | 26.4 | +17% |

CONCLUSION

A significant increase in the amount of drink consumed over the course of the study is observed for all the batches, i.e. the batches: polydextrose/erythritol, Nutriose® FB17/erythritol, Nutriose® FB17/mannitol. This increase is very large from the beginning of the study and continues up to the end of the study. Increases in consumption ranging from +10% to +33% are observed for these batches over the entire study and in comparison with the control batch.

The measurement of diuresis shows that these same mixtures bring about a very large increase in the volume of urine excreted from the beginning of the study and throughout the study. Compared with the control batch, these increases are of the order of +14% to +54% over the total volume at the end of the study, compared with the control batch.

The drink consumption and diuresis results demonstrate a very close link between these two parameters. The appetence-inducing agents in the study very definitely lead to an increase in water consumption and therefore in the volume of urine excreted; this second phenomenon is accentuated by the effect of the diuretic agents tested.

It is understood that the doses tested in rats may be greater than the doses that can be administered to cats or dogs depending on their intestinal tolerance; they are, in this case, only meant to be illustrative.

The invention claimed is:

1. A method for treating urolithiasis, comprising orally administering an effective amount of an osmotic diuretic agent and an effective amount of an appetence-inducing agent selected from the group consisting of indigestible dextrins, polydextrose and a mixture thereof to a subject in need thereof, said amounts being effective to treat urolithiasis in said subject.

2. The method of claim 1, wherein the effective amount of said osmotic diuretic agent and the effective amount of said appetence-inducing agent are administered simultaneously or sequentially to said subject in need thereof.

3. The method of claim 1, wherein said subject in need thereof is a human, a cat or a dog.

4. The method of claim 1, wherein said osmotic diuretic agent is a polyol or a mixture of polyols.

5. The method of claim 4, wherein said polyol or mixture of polyols is selected from the group consisting of mannitol, erythritol, arabitol, isosorbide, and any mixtures thereof.

6. The method according to claim 1, wherein said osmotic diuretic agent and said appetence-inducing agent are administered as a composition comprising said effective amount of an osmotic diuretic agent and an effective amount of said appetence-inducing agent to a subject in need thereof.

7. The method of claim 6, wherein said composition is a low-calorie composition.

8. The method according to claim 6, wherein said composition is a drink, a tablet or a powder.

9. The method according to claim 6, wherein the diuretic agent/appetence-inducing agent weight ratio is between 1:50 and 50:1.

10. The method according to claim 6, wherein the diuretic agent/appetence-inducing agent weight ratio is between 1:20 and 20:1.

11. The method according to claim 6, wherein the diuretic agent/appetence-inducing agent weight ratio is between 1:2 and 1:3.

12. The method of claim 6, wherein said subject in need thereof is a human, a cat or a dog.

13. The method of claim 6, wherein said osmotic diuretic agent is a polyol or a mixture of polyols.

14. The method of claim 6, wherein said polyol or mixture of polyols is selected from the group consisting of mannitol, erythritol, arabitol, isosorbide, and any mixtures thereof.

15. The method of claim 1, wherein
said effective amount of said osmotic diuretic agent is 1 to 50 grams per liter administered to said subject, and
said effective amount of said appetence-inducing agent is 2 to 20 grams per liter administered to said subject.

* * * * *